United States Patent
Hara et al.

(10) Patent No.: US 12,053,842 B2
(45) Date of Patent: Aug. 6, 2024

(54) WELD INSPECTION APPARATUS

(71) Applicant: JFE STEEL CORPORATION, Tokyo (JP)

(72) Inventors: Asato Hara, Tokyo (JP); Syoma Murakami, Tokyo (JP); Yasushi Kitani, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 92 days.

(21) Appl. No.: 17/778,583

(22) PCT Filed: Oct. 14, 2020

(86) PCT No.: PCT/JP2020/038690
§ 371 (c)(1),
(2) Date: May 20, 2022

(87) PCT Pub. No.: WO2021/106400
PCT Pub. Date: Jun. 3, 2021

(65) Prior Publication Data
US 2023/0001519 A1 Jan. 5, 2023

(30) Foreign Application Priority Data
Nov. 27, 2019 (JP) .................. 2019-213856

(51) Int. Cl.
*B23K 31/00* (2006.01)
*B23K 31/12* (2006.01)
(Continued)

(52) U.S. Cl.
CPC ......... *B23K 31/125* (2013.01); *G01N 33/207* (2019.01); *H04N 23/90* (2023.01);
(Continued)

(58) Field of Classification Search
CPC ............ B23K 2101/006; B23K 31/125; B23K 26/082; G01N 33/207
See application file for complete search history.

(56) References Cited

U.S. PATENT DOCUMENTS

2017/0081000 A1* 3/2017 Cioanta .................. B08B 3/024
2018/0194087 A1* 7/2018 Dan ........................ G01M 3/08
(Continued)

FOREIGN PATENT DOCUMENTS

| CN | 104823043 A | 8/2015 |
| CN | 106990111 A | 7/2017 |

(Continued)

OTHER PUBLICATIONS

JP2000-180384 computer English translation (Year: 2023).*

(Continued)

*Primary Examiner* — Erin B Saad
(74) *Attorney, Agent, or Firm* — Oliff PLC

(57) ABSTRACT

A weld inspection apparatus that detects a weld defect in a welded portion of metal plates and includes a liquid application head disposed over one side surface of the metal plates and capable of moving in a welding direction of the metal plates, and an air jet head disposed over another side surface of the metal plates and capable of moving in the welding direction of the metal plates. The liquid application head includes a liquid application nozzle that projects toward the one side surface of the metal plates and applies liquid for sealing the welded portion. The air jet head includes an air jet nozzle that projects toward the another side surface of the metal plates and discharges air toward the welded portion to which the liquid has been applied.

16 Claims, 3 Drawing Sheets

(51) Int. Cl.
*G01N 33/207* (2019.01)
*H04N 23/90* (2023.01)
*B23K 101/00* (2006.01)
*B23K 101/18* (2006.01)
*B23K 103/04* (2006.01)

(52) U.S. Cl.
CPC .... *B23K 2101/006* (2018.08); *B23K 2101/18* (2018.08); *B23K 2103/04* (2018.08)

(56) References Cited

U.S. PATENT DOCUMENTS

| | | | | |
|---|---|---|---|---|
| 2022/0196569 A1* | 6/2022 | Sato | ...................... | B23K 31/125 |
| 2023/0001519 A1* | 1/2023 | Hara | ....................... | B23K 26/32 |

FOREIGN PATENT DOCUMENTS

| | | | |
|---|---|---|---|
| EP | 2 927 672 A1 | 10/2015 | |
| EP | 3 176 537 A1 | 6/2017 | |
| JP | S60-3535 A | 1/1985 | |
| JP | 2000-35372 A | 2/2000 | |
| JP | 2000-180384 A | 6/2000 | |
| JP | 2001-066213 A | 3/2001 | |
| JP | 2002-139398 A | 5/2002 | |
| JP | 2006-167676 A | 6/2006 | |
| JP | 2008-196866 A | 8/2008 | |
| JP | 2008-279497 A | 11/2008 | |
| JP | 2013-34999 A | 2/2013 | |
| JP | 3182190 U | 3/2013 | |
| JP | 3194227 U | 11/2014 | |

OTHER PUBLICATIONS

Nov. 14, 2022 Search Report issued in European Patent Application No. 20893061.0.
Jul. 10, 2023 Office Action issued in Chinese Patent Application No. 2020800808835.
Nov. 17, 2020 International Search Report issued in International Application No. PCT/JP2020/038690.
May 6, 2023 Office Action issued in Chinese Patent Application No. 202080080883.5.
Feb. 13, 2023 Office Action issued in Chinese Patent Application No. 202080080883.5.
Apr. 19, 2022 Office Action issued in Japanese Patent Application No. 2021-507714.
Aug. 23, 2022 Office Action issued in Japanese Patent Application No. 2021-507714.
May 16, 2024 Office Action issued in Korean Patent Application No. 2022-7017103.

* cited by examiner

WELD INSPECTION APPARATUS

TECHNICAL FIELD

This application relates to a weld inspection apparatus that enables simple and accurate detection of a weld defect.

BACKGROUND

Welding has been commonly used to join structural members. However, various weld defects may occur during a welding process.

When, for example, steel sheets are welded together, a weld defect referred to as a crack that extends through a welded portion may occur. The weld defect has an adverse influence on airtightness and corrosion resistance of a product. Accordingly, the weld defect needs to be detected on-line by, for example, an image recognition device, and then a countermeasure, such as re-welding, needs to be taken.

In recent years, steel sheets have often been alloyed to increase the strength thereof, and narrow seem welding, typically laser welding, has been put to practical use. In such a case, a weld defect, such as a crack, that is so small that it cannot be detected by an on-line inspection method according to the related art may occur.

The weld defect may be more precisely detected off-line by, for example, a cross-section observation test, a liquid penetrant test, or a radiographic test. The cross-section observation test enables accurate detection but requires high temporal and operational costs because the welded portion needs to be cut out. The liquid penetrant test can be performed in a shorter time than the cross-section observation test, but still takes a long time. In addition, when the welded portion is formed by, for example, laser welding and has a narrow width and a large underfill region, it cannot be accurately determined whether the welded portion is defective. The radiographic test requires high-energy radiation, and it is necessary to prevent radiation leakage by using a large detection device. Therefore, it is difficult to carry out the radiographic test in a factory.

Patent Literatures 1 and 2 given below are examples of known documents that disclose methods for detecting a defect, such as a crack, in a welded portion formed by laser welding.

The technology disclosed in Patent Literature 1 utilizes the fact that the width of a heat-affected zone decreases when a weld bead has a weld crack. A threshold is set for the width of the heat-affected zone, and it is determined that defective welding has occurred if it is determined by image recognition that the width is below the threshold. The technology disclosed in Patent Literature 2 utilizes the fact that when a weld bead has a weld crack, an internal space of the crack serves as a heat insulating layer and delays cooling of the cracked portion. A temperature history is measured at a location distant from the welded portion, and it is determined that defective welding has occurred when a cooling rate is below a certain threshold.

CITATION LIST

Patent Literature

PTL 1: Japanese Unexamined Patent Application Publication No. 2008-196866

PTL 2: Japanese Unexamined Patent Application Publication No. 2008-279497

SUMMARY

Technical Problem

As described above, the welded portion formed by, for example, laser welding tends to have a smaller width, and the size of the weld defect decreases as the width of the welded portion decreases. Accordingly, a normal welded portion and a welded portion having a weld crack or the like have a smaller difference in the width of the heat-affected zone or a smaller difference in temperature variation. Therefore, whether a welded portion is defective cannot be accurately determined based on the threshold for the width of the heat-affected zone as described in Patent Literature 1 or based on the threshold for the temporal variation of temperature as described in Patent Literature 2.

The disclosed embodiments have been made in light of the above-described problems, and an object of the disclosed embodiments is to provide a weld inspection apparatus capable of performing a simple and accurate on-line detection of a small weld defect in a welded portion.

Solution to Problem

The solutions to the above-described problems are as follows:

[1] A weld inspection apparatus that detects a weld defect in a welded portion of a metal plate, the weld inspection apparatus including:

a liquid application head disposed over one side surface of the metal plate and capable of moving in a welding direction of the metal plate; and an air jet head disposed over another side surface of the metal plate and capable of moving in the welding direction of the metal plate, wherein the liquid application head includes a liquid application nozzle that projects toward the one side surface of the metal plate and applies liquid for sealing the welded portion, and wherein the air jet head includes an air jet nozzle that projects toward the another side surface of the metal plate and discharges air toward the welded portion to which the liquid has been applied.

[2] The weld inspection apparatus according to [1], wherein the liquid application head includes a camera at a location in advance of the liquid application nozzle in a moving direction, the camera capturing an image of the welded portion.

[3] The weld inspection apparatus according to [1] or [2], wherein the air jet head includes a camera at a location in advance of the air jet nozzle in a moving direction, the camera capturing an image of the welded portion.

[4] The weld inspection apparatus according to any one of [1] to [3], wherein the liquid application nozzle is disposed in advance of the air jet nozzle in a moving direction.

[5] The weld inspection apparatus according to any one of [1] to [4], wherein the liquid application head includes a rear camera at a location behind the liquid application nozzle in a moving direction, the rear camera capturing an image of a bubble formed in the liquid.

Advantageous Effects

According to the disclosed embodiments, the weld defect is detected by utilizing the fact that bubbles are formed in the liquid applied to one side surface of the metal plate when air discharged from the another side surface of the metal plate passes through the weld defect. Thus, simple and accurate detection of the weld defect can be performed even when the weld defect is small.

In addition, on-line detection is possible because the liquid application head and the air jet head are movable in the welding direction. Accordingly, the inspection time can be greatly reduced compared with that in the case of using an off-line detection device or an off-line detection method.

DETAILED DESCRIPTION

Disclosed embodiments will now be described with reference to the drawings. The disclosure is not intended to be limited to these specific embodiments.

Figure 1:
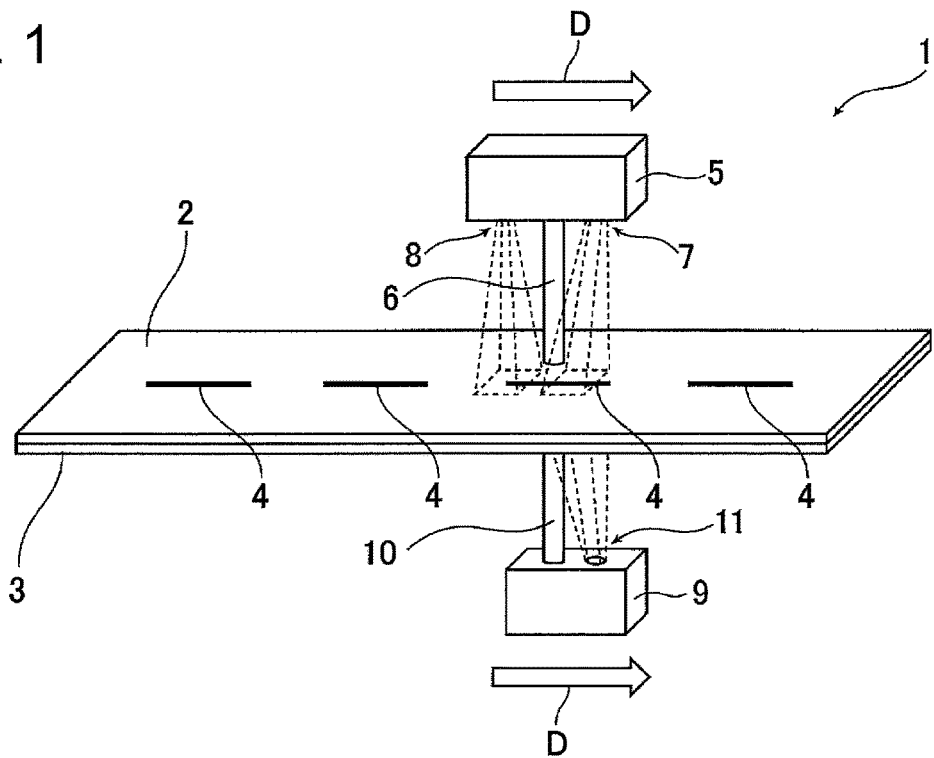
FIG. 1 is a perspective view illustrating an example of a weld inspection apparatus according to an embodiment.

FIG. 1 shows an example in which a metal plate 2 and a metal plate 3 are stacked on top of each other and lap-welded together by forming a plurality of welded portions 4 in a longitudinal direction of the metal plates 2 and 3. Welding is generally performed in one direction, and this direction is referred to as a welding direction. The welding direction coincides with the longitudinal direction of the welded portions 4, and also coincides with the longitudinal direction of the metal plates 2 and 3 in the example illustrated in FIG. 1. Lap welding is generally performed by laser welding, and therefore a small weld defect easily occurs. The weld defect cannot be easily detected by a weld inspection method according to the related art.

<Weld Inspection Apparatus>

Figure 2:
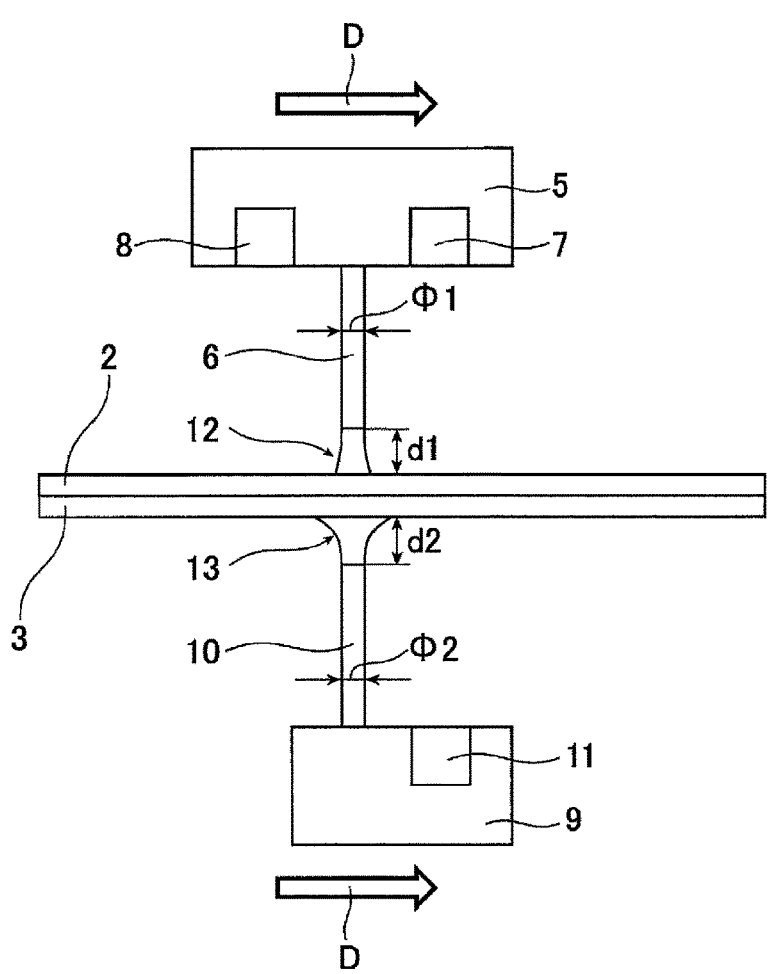
FIG. 2 is a side view illustrating the example of the weld inspection apparatus according to an embodiment.

As illustrated in FIG. 1, a weld inspection apparatus 1 according to the disclosed embodiments includes a liquid application head 5 and an air jet head 9. The liquid application head 5 includes a cylindrical liquid application nozzle 6 that projects toward one side surface (front side) of the metal plates. The air jet head 9 includes a cylindrical air jet nozzle 10 that projects toward another side surface (back side) of the metal plates. As illustrated in FIG. 2, the liquid application nozzle 6 applies liquid 12 to a front surface of the metal plate 2, and the air jet nozzle 10 discharges air 13 toward a back surface of the metal plate 3.

The liquid application head 5 and the air jet head 9 move in the welding direction. In FIG. 1, the direction in which the liquid application head 5 and the air jet head 9 move is referred to as a moving direction D. The liquid application head 5 and the air jet head 9 preferably move in synchronization with each other. In such a case, the inspection time can be reduced, and there is no risk that the liquid will be evaporated due to a time lag between the application of the liquid and the movement of the air jet head and accurate detection of a crack cannot be performed.

The air jet nozzle 10 discharges air against the welded portions 4 to which the liquid has been applied by the liquid application nozzle 6. To reliably apply the liquid before the air is discharged, the liquid application nozzle 6 is preferably disposed in advance of the air jet nozzle 10 in the moving direction.

As described in detail below, when the air 13 is discharged from the back side of each welded portion 4 to which the liquid 12 has been applied, if there is a weld defect, bubbles are found in the liquid on the front side of the welded portion 4. Whether or not a weld defect is present can be determined based on whether or not the bubbles are present.

The liquid application head 5 preferably has a camera 7 at a location in advance of the liquid application nozzle 6 in the moving direction. The air jet head 9 preferably has a camera 11 at a location in advance of the air jet nozzle 10 in the moving direction. The camera 7 and the camera 11 may each be any device capable of recognizing the welded portions 4 based on, for example, brightness information of a captured image. In one example, the camera 7 and the camera 11 respectively capture an image of the front surface of the metal plate 2 and an image of the back surface of the metal plate 3, and then output the captured images to a control device (not shown). The control device processes the images to determine the position of each welded portion 4, and then controls the operations of the liquid application head 5 and the air jet head 9. More specifically, the control device causes the liquid application head 5 and the air jet head 9 to move in the welding direction of the welded portions 4. The camera 7, the camera 11, and the control device may be integrated with each other.

The liquid application head 5 preferably has a rear camera 8 at a location behind the liquid application nozzle 6 in the moving direction. The rear camera 8 captures an image of the front side of each welded portion 4 when air is discharged from the back side of the welded portion. The image captured by the rear camera 8 may be displayed on a display device (not illustrated). Alternatively, the control device may determine whether there are bubbles in the liquid on the front surface of the welded portion 4 based on the captured image, and thereby determine whether a weld defect is present. In such a case, automatic detection of a weld defect can be performed.

The rear camera 8 is preferably disposed at a position corresponding to that of the air jet nozzle 10 (position at which the rear camera 8 faces the air jet nozzle 10) in the moving direction at least during the inspection. In such a case, the rear camera 8 is capable of reliably capturing the image of the welded portion 4 toward which the air is being discharged.

As described above, the function of following the welded portions 4 provided by the camera 7 or the camera 11 and the function of determining whether the bubbles are present provided by the rear camera 8 may be combined to realize automatic inspection of the welded portions 4.

The operation of the weld inspection apparatus 1 will now be described in more detail with reference to FIGS. 1 and 2. First, the liquid application head 5 applies the liquid 12 to the front surface of one of the welded portions 4 along the welding direction while moving in the moving direction D at the front side of the metal plate 2. Next, the air jet head 9 discharges the air 13 from the back side of the welded portion 4 to which the liquid 12 has been applied. The air jet head 9 may discharge the air 13 while moving in the moving direction D to reduce the inspection time. Alternatively, the movement of the air jet head 9 may be stopped when the air 13 is discharged to perform high-accuracy inspection. Whether the bubbles are present may be determined either by visual observation or based on the image captured by the rear camera 8. In the case where the captured image is used, to reliably capture the image of the welded portion 4 toward which the air is being discharged, the rear camera 8 is disposed so that the image capture field of view thereof in the moving direction D covers the position at which the air 13 is discharged from the air jet nozzle 10 at the back side.

Figure 3:
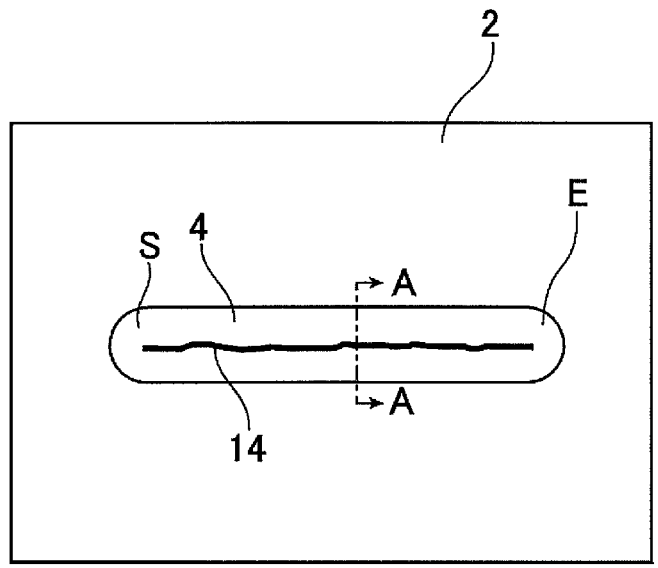
FIG. 3 is a top view of a weld joint having a weld defect.
Figure 4:
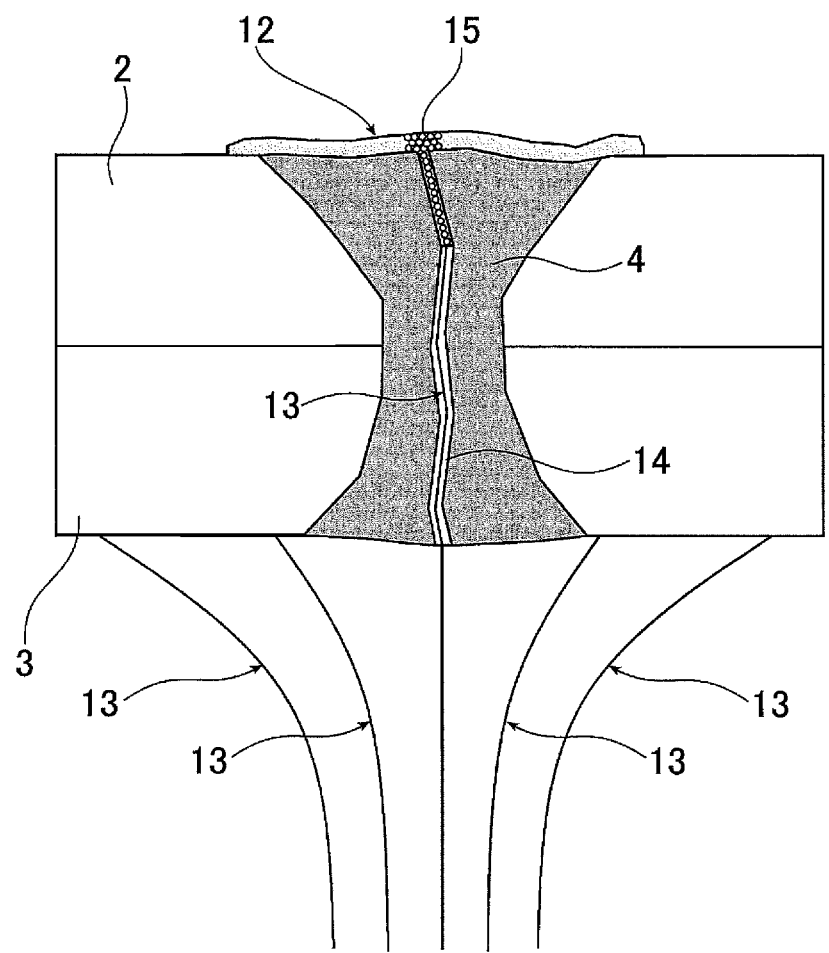
FIG. 4 is a sectional view of the weld joint illustrated in FIG. 3 taken along line A-A.

The principle of detection of a weld defect by the weld inspection apparatus according to the disclosed embodiments will now be described with reference to FIGS. 3 and 4. FIG. 3 is a top view of a region including one of the welded portions 4, and FIG. 4 is a sectional view of FIG. 3 taken along line A-A. FIG. 4 shows a weld defect 14 in the welded portion 4 that is being detected by discharging the air 13. According to the disclosed embodiments, the welded portion 4 includes a melted portion that corresponds to a portion in which a base material was melted during welding, and a heat-affected zone (HAZ) that surrounds the melted portion and in which the microstructure has been changed due to welding heat. As illustrated in FIG. 3, the weld defect 14 often extends entirely from a welding starting end portion S to a welding terminating end portion E.

First, the liquid 12 for sealing the welded portion 4 is applied to the front side of the welded portion 4. The liquid 12 may be any liquid that has a surface tension high enough to seal the front surface of the welded portion 4 and that allows bubbles to be formed when the air is discharged. The liquid 12 may be, for example, liquid containing a surface active agent or a bubble forming agent, such as a macromolecular compound, and examples thereof include known liquid used for gas leak detection.

Next, the air 13 is discharged from the back side of the metal plate 3 toward the welded portion 4 to which the liquid 12 has been applied. When the welded portion 4 has the weld defect 14 (more specifically, a crack extending entirely through the welded portion in the plate thickness direction) as in the example illustrated in FIGS. 3 and 4, the air 13 passes through the weld defect 14 and reaches the front side of the metal plate 2. Bubbles 15 are generated when the air 13 passes through the liquid 12 at the front side of the welded portion 4.

When the welded portion 4 has no weld defects, for example, when the welded portion 4 has no cracks that extend entirely through the welded portion 4 in the thickness direction, the air 13 discharged from the back side of the metal plate 3 does not reach the front side of the metal plate 2, and no bubbles 15 are formed in the liquid 12.

As described above, the air 13 is discharged from the back side of the welded portion 4, and whether or not the weld defect 14 is present is determined based on whether or not the bubbles 15 are present in the liquid 12 at the front side of the welded portion 4. Thus, whether or not a small weld defect is present can be determined by observing whether the bubbles are present, and the detection of defects is simpler and more accurate as compared to the related art. In addition, since the detection can be performed on-line, the detection can be performed in a significantly shorter time as compared to the related art. In particular, when the above-described weld inspection apparatus is applied to, for example, a welded portion of alloyed steel sheets or a welded portion formed by laser welding, even a small weld defect can be reliably detected.

Whether the weld defect 14 is present can be more accurately determined by cutting the welded portion 4 along a plane perpendicular to the welding direction and observing the cut surface with, for example, an optical microscope after the weld defect detection using the above-described weld inspection apparatus.

Preferred conditions of the weld inspection apparatus will now be described. The disclosed embodiments are not intended to be limited to the preferred conditions described below.

<Viscosity of Liquid 12: $\mu$ (Pa·s)>

When the liquid 12 has a high viscosity, the air 13 may be blocked by the liquid 12 and unable to pass through the weld defect 14. When the liquid 12 has a low viscosity, the air 13 discharged toward the metal plates 2 and 3 having the weld defect 14 extending therethrough in the thickness direction may pass through the liquid 12 applied to the front surface of the welded portion 4 without forming bubbles in the liquid 12. Accordingly, the viscosity $\mu$ of the liquid 12 is preferably 0.003 Pa·s or more and 1 Pa·s or less, and more preferably in the range of 0.005 Pa·s or more and 0.5 Pa·s or less.

<Amount of Liquid 12 Applied: A (ml/mm$^2$)>

When the amount of the liquid 12 applied is small, the liquid 12 may fail to spread over the entire front surface of the welded portion 4 to completely seal the front surface of the welded portion 4. In such a case, there is a possibility that no bubbles 15 are formed and the weld defect 14 cannot be detected due to the air 13 passing through a region in which the liquid 12 is not applied. When the amount of the liquid 12 applied is large, the liquid 12 may flow away from the welded portion 4 and fail to seal the front surface of the welded portion 4. Accordingly, the amount a of the liquid 12 applied to the welded portion 4 per unit surface area is preferably 0.0001 ml/mm$^2$ or more and 0.003 ml/mm$^2$ or less, and more preferably in the range of 0.0005 ml/mm$^2$ or more and 0.002 ml/mm$^2$ or less.

<Diameter of Liquid Application Nozzle 6: $\Phi 1$ (Mm)>

When the liquid application nozzle 6 has a small diameter, there is a possibility that an end of the nozzle will be clogged. When the liquid application nozzle 6 has a large diameter, the inner diameter of the nozzle may be greater than the width of the welded portion 4, and there is a possibility that the liquid 12 will flow outward from the welded portion 4. Accordingly, the diameter $\Phi 1$ of the liquid application nozzle is preferably 0.1 mm or more and 5.0 mm or less, and more preferably in the range of 0.5 mm or more and 3 mm or less.

<Distance Between Liquid Application Nozzle 6 and Front Surface of Metal Plate 2: d1 (mm)>

When the distance d1 is small, the liquid 12 that is in contact with the metal plate 2 may interfere with the liquid 12 that is subsequently supplied, and there is a possibility that the liquid 12 cannot be appropriately supplied from the liquid application nozzle 6. When the distance d1 is large, there is a possibility that the liquid 12 cannot be applied at a desired location. Accordingly, the distance d1 between the liquid application nozzle 6 and the front surface of the metal plate 2 is preferably 1.0 mm or more and 5.0 mm or less, and more preferably in the range of 1.5 mm or more and 4 mm or less.

<Supply Speed of Liquid 12: V (mm/s)>

When the liquid 12 is supplied at a low supply speed, it takes a long time to apply the liquid 12. When the liquid 12 is supplied at a high supply speed, the liquid 12 may spatter on the front surface of the welded portion 4, and there is a possibility that the front surface cannot be sealed appropriately. Accordingly, the supply speed V of the liquid 12 is preferably 1.0 mm/s or more and 1000 mm/s or less, and more preferably in the range of 5.0 mm/s or more and 100 mm/s or less.

<Amount of Air 13 Supplied: b (ml/min)>

When the amount of the air 13 supplied is small, even if there is the weld defect 14 that extends through the welded portion in the plate thickness direction, there is a possibility that the air 13 will fail to pass through the weld defect 14. When the amount of the air 13 supplied is large, there is a possibility that the air 13 will blow off the liquid 12 on the front surface of the metal plate and the weld defect 14 cannot be detected. Accordingly, the amount b of the air 13 supplied is preferably 10 ml/min or more and 50 ml/min or less, and more preferably in the range of 15 ml/min or more and 40 ml/min or less.

<Angle Between Air Jet Nozzle 10 and Metal Plate 3 at Back Side: θ (Deg)>

When the angle θ is less than 30°, the air 13 cannot easily pass through the weld defect 14, and there is a possibility that the weld defect 14 cannot be detected. To facilitate passing of the air 13 through the weld defect 14, θ is preferably close to 90°. Therefore, θ described above is preferably 30° or more and 90° or less, and more preferably in the range of 45° or more and 90° or less. When θ described above is calculated, the direction in which the air jet nozzle 10 is inclined is not particularly limited.

<Inner Diameter of Air Jet Nozzle 10: Φ2 (mm)>

When the inner diameter Φ2 is small, it is difficult to detect the weld defect 14 if the air 13 is discharged toward a position displaced from the weld defect 14. When Φ2 described above is large, there is a possibility that the air 13 cannot be discharged at a sufficient pressure. Therefore, the air 13 may fail to pass through the weld defect 14 that extends through the welded portion in the plate thickness direction, and it may be difficult to detect the weld defect 14. Accordingly, Φ2 is preferably 0.1 mm or more and 5.0 mm or less, and more preferably in the range of 1.0 mm or more and 4.0 mm or less.

<Distance Between Air Jet Nozzle 10 and Metal Plate 3 at Back Side: d2 (mm)>

When the distance d2 is small, it is difficult to detect the weld defect 14 if the air 13 is discharged toward a position displaced from the weld defect 14. When d2 described above is large, the air 13 may spread before reaching the back surface of the metal plate 3. Therefore, the pressure may be insufficient, and it may be difficult to detect the weld defect 14. Accordingly, d2 is preferably 1.0 mm or more and 5.0 mm or less, and more preferably in the range of 1.5 mm or more and 4.0 mm or less.

<Inspection Object>

Figure 5:
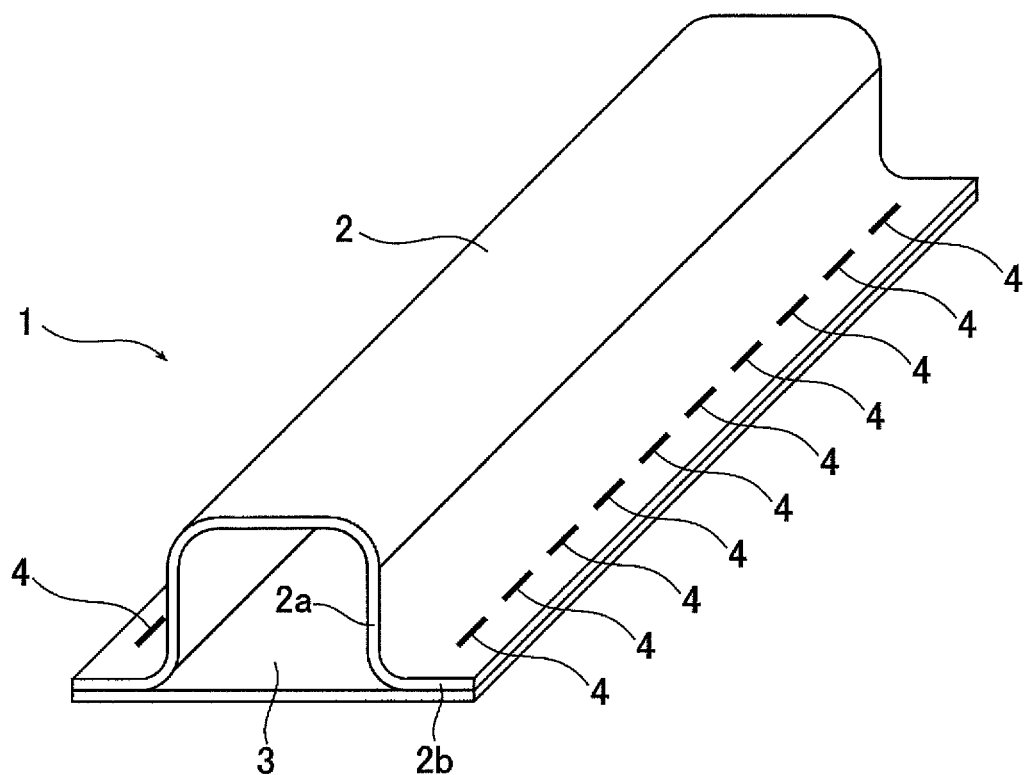
FIG. 5 is a perspective view of a skeletal component for an automobile, which is an example of an inspection object.

A skeletal component for an automobile is an example of an inspection object to which the weld inspection apparatus according to the disclosed embodiments can be applied. FIG. 5 illustrates an example of a skeletal component for an automobile. FIG. 5 shows a steel sheet 2 that serves as a frame component that is substantially hat-shaped in cross section, and a steel sheet 3 that serves as a panel component. The skeletal component for an automobile has a closed cross section formed by welding flanges 2b of the frame component (steel sheet 2) to portions of the panel component (steel sheet 3) that face the flanges 2b.

The above-described skeletal component for an automobile may be, for example, a center pillar or a roof rail. These components are generally formed of high tension steel sheets, and the flanges are often lap-welded by laser welding. Therefore, it is likely that small weld defects will be formed. The weld inspection apparatus according to the disclosed embodiments enables simple and accurate detection of such a small weld defect.

Examples

The operation and effects of the disclosed embodiments will now be described by way of an example. The disclosed embodiments are not limited to the example described below.

In this example, steel sheets having chemical compositions shown in Table 1 were used as test pieces. More specifically, two steel sheets having a chemical composition of steel type A or B were lap-welded together. The thickness of the steel material was 1.2 mm, 1.6 mm, or 2.0 mm for steel type A, and was 1.6 mm for steel type B. The steel sheet 2 and the steel sheet 3 that were lap-welded together had the same thickness. The steel sheets 2 and 3 both had a length of 500 mm in the longitudinal direction. As illustrated in FIG. 5, the steel sheet 2 included vertical wall portions 2a and the flanges 2b, and was hat-shaped. The steel sheet 2 and the steel sheet 3 were lap-welded together in the same manner as illustrated in FIG. 5. More specifically, the hat-shaped steel sheet 2 and a bottom sheet (steel sheet 3) were stacked together, and then welded portions 4 were formed by intermittently performing laser welding from the front side of the flanges 2b of the steel sheet 2 in the stacked state at a plurality of positions (20 positions) along the longitudinal direction. To evaluate the effectiveness of the detection of weld defects, welding was performed so that weld defects were formed in all of the welded portions 4 at the 20 positions. With regard to the size of the test specimen, the height of the vertical wall portions 2a was 40 mm, the length of the flanges 2b in the longitudinal direction was 500 mm, and the width of the flange 2b at each side was 20 mm.

The weld defects were detected by the following procedure.

(1) The liquid 12 was applied to each of the welded portions 4, which were formed on the flanges of the hat-shaped test specimen at the 20 positions, from the front side, and the air 13 was discharged from the back side. Then, it was determined whether the bubbles 15 were formed in the liquid 12.

(2) Each of the welded portions 4 at the 20 positions was cut along a plane perpendicular to the welding direction at a position that is 5 mm from the welding terminating end portion E, and the cut surface was observed.

(3) The detection was evaluated as successful if the welding positions at which bubbles were generated in the liquid 12 on the front surface in (1) matched the welding positions at which the weld defect 14 was found in (2) at all of the 20 positions, and was evaluated as unsuccessful if there is a mismatch at one or more of the 20 positions. The obtained results are shown in Table 2.

TABLE 1

| Steel Type | Strength (MPa) | Composition (mass %) | | | | | | | | | | | |
|---|---|---|---|---|---|---|---|---|---|---|---|---|---|
| | | C | Si | Mn | P | S | Ti | Nb | Cr | Mo | B | Al | N |
| A | 980 | 0.21 | 1.5 | 2.0 | 0.004 | 0.0007 | — | — | — | — | — | 0.031 | 0.0025 |
| B | 1180 | 0.18 | 1.4 | 2.7 | 0.003 | 0.0009 | — | — | — | — | — | 0.025 | 0.0035 |

Balance is Fe and Unavoidable Impurities

TABLE 2

| No. | Steel Type | TS (MPa) | Thickness of Steel Sheet 2 t2 (mm) | Thickness of Steel Sheet 3 t3 (mm) | Total Thickness T (mm) | Liquid Viscosity μ (Pa·s) | Amount of Liquid Applied a (ml/mm²) | Liquid Nozzle Diameter Φ1 (mm) | Distance between Liquid Nozzle and Steel Sheet 2 d1 (mm) |
|---|---|---|---|---|---|---|---|---|---|
| 1 | A | 980 | 1.2 | 1.2 | 2.4 | 0.1 | 0.001 | 2.0 | 2.0 |
| 2 | A | 980 | 1.6 | 1.6 | 3.2 | 0.1 | 0,001 | 2.0 | 2.0 |
| 3 | A | 980 | 2.0 | 2.0 | 4.0 | 0.1 | 0.001 | 2.0 | 2.0 |
| 4 | B | 1180 | 1.6 | 1.6 | 3.2 | 0.1 | 0.001 | 2.0 | 2.0 |

| No. | Liquid Supply Speed V (mm/s) | Amount of Air Supplied b (ml/min) | Air Supply Angle θ (deg) | Air Nozzle Diameter Φ2 (mm) | Distance between Air Nozzle and Steel Sheet 3 d2 (mm) | Weld defect Detection Result | Remarks |
|---|---|---|---|---|---|---|---|
| 1 | 10 | 25 | 90 | 2.0 | 2.0 | O | Example |
| 2 | 10 | 25 | 90 | 2.0 | 2.0 | O | Example |
| 3 | 10 | 25 | 90 | 2.0 | 2.0 | O | Example |
| 4 | 10 | 25 | 90 | 2.0 | 2.0 | O | Example |

O: Successful
x: Unsuccessful

As shown in Table 2, Nos. 1 to 4 according to the examples of the disclosed embodiments all satisfied the above-described preferred conditions, and the weld defects were more accurately detected. More specifically, the liquid viscosity μ was 0.1 Pa·s for Nos. 1 to 4, and satisfied the condition of 0.003 Pa·s or more and 1 Pa·s or less. Accordingly, the air 13 passed through the liquid 12 on the hat-shaped metal plate 2 and formed bubbles in the liquid 12 applied to the front surface of each welded portion 4.

The amount a of the liquid 12 applied was 0.001 ml/mm² for Nos. 1 to 4, and satisfied the condition of 0.0001 ml/mm² or more and 0.003 ml/mm² or less. Accordingly, the liquid 12 was applied to each welded portion 4 over the entire area thereof to completely seal the front surface of the welded portion 4.

In addition, Φ1 of the liquid nozzle 6 was 2.0 mm for Nos. 1 to 4, and satisfied the condition of 0.1 mm or more and 5.0 mm or less. Accordingly, the liquid nozzle 6 was not clogged, and the liquid 12 was reliably prevented from flowing outward from the welded portions 4.

The distance d1 between the liquid nozzle 6 and the metal plate 2 was 2.0 mm for Nos. 1 to 4, and satisfied the condition of 1.0 mm or more and 5.0 mm or less. Accordingly, the liquid 12 did not interfere with the liquid 12 supplied at a different timing, and formation of regions in which no liquid 12 was applied to the welded portions 4 was prevented.

The supply speed V of the liquid 12 was 10 mm/s for Nos. 1 to 4, and satisfied the condition of 1.0 mm/s or more and 1000 mm/s or less. Accordingly, it was possible to seal each welded portion 4 with the liquid 12 within a shortened application time.

The amount b of the air 13 supplied was 25 ml/min for Nos. 1 to 4, and satisfied the condition of 10 ml/min or more and 50 ml/min or less. The supply angle θ of the air 13 was 90°, and satisfied the condition of 30° or more and 90° or less. Accordingly, the air 13 reliably passed through the weld defect 14 and generated the bubbles 15.

The diameter Φ2 of the air jet nozzle 10 was 2.0 mm for Nos. 1 to 4, and satisfied the condition of 0.1 mm or more and 5.0 mm or less. The distance d2 between the air jet nozzle 10 and the metal plate 3 was 2.0 mm for Nos. 1 to 4, and satisfied the condition of 1.0 mm or more and 5.0 mm or less. Accordingly, the air 13 was discharged at a sufficient pressure without being displaced from the weld defect 14, and generated the bubbles 15.

As described above, whether the weld defect 14 was present was accurately determined for Nos. 1 to 4, which are examples of the disclosed embodiments that satisfied all of the preferred conditions.

The disclosure is not limited to the above-described embodiments, and various changes are possible. For example, although welded portions of metal plates made of a steel material, such as a high tension steel, are inspected in the above-described embodiment, disclosed embodiments are not limited to this, and can be applied also to inspections of welded portions of metal plates made of, for example, mild steel, coated steel sheets, stainless steel, heat-resisting steel, or aluminum alloy. Accordingly, the welding method is not limited to the above-described laser welding, and various known welding methods suitable for the types of the metal plates may be used. In addition, although the weld inspection apparatus 1 is used for inspection of lap welding, the weld inspection apparatus 1 may also be applied to inspection of butt welding.

The invention claimed is:

1. A weld inspection apparatus that detects a weld defect in a welded portion of a metal plate for an automobile frame part, the weld inspection apparatus comprising:
    a liquid application head disposed over one side surface of the metal plate and configured to move in a welding direction of the metal plate; and
    an air jet head disposed over another side surface of the metal plate and configured to move in the welding direction of the metal plate,
    wherein the liquid application head comprises a liquid application nozzle that projects toward the one side surface of the metal plate and applies liquid for sealing the welded portion,
    the air jet head comprises an air jet nozzle that projects toward the another side surface of the metal plate and discharges air toward the welded portion to which the liquid has been applied,
    the liquid application head and the air jet head are disposed at positions corresponding to each other with the metal plate interposed therebetween, and are configured to advance in a welding direction of the metal plate in synchronization with each other, and
    an application amount of the liquid is in a range of 0.0001 ml/mm$^2$ or more and 0.003 ml/mm$^2$ or less.

2. The weld inspection apparatus according to claim 1, wherein the liquid application head further comprises a camera disposed at a location in advance of the liquid application nozzle in a moving direction, the camera configured to capture an image of the welded portion.

3. The weld inspection apparatus according to claim 1, wherein the air jet head further comprises a camera disposed at a location in advance of the air jet nozzle in a moving direction, the camera configured to capture an image of the welded portion.

4. The weld inspection apparatus according to claim 1, wherein the liquid application nozzle is disposed in advance of the air jet nozzle in a moving direction.

5. The weld inspection apparatus according to claim 1, wherein the liquid application head further comprises a rear camera disposed at a location behind the liquid application nozzle in a moving direction, the rear camera configured to capture an image of a bubble formed in the liquid.

6. The weld inspection apparatus according to claim 2, wherein the air jet head further comprises a camera disposed at a location in advance of the air jet nozzle in the moving direction, the camera configured to capture an image of the welded portion.

7. The weld inspection apparatus according to claim 2, wherein the liquid application nozzle is disposed in advance of the air jet nozzle in the moving direction.

8. The weld inspection apparatus according to claim 3, wherein the liquid application nozzle is disposed in advance of the air jet nozzle in the moving direction.

9. The weld inspection apparatus according to claim 6, wherein the liquid application nozzle is disposed in advance of the air jet nozzle in the moving direction.

10. The weld inspection apparatus according to claim 2, wherein the liquid application head further comprises a rear camera disposed at a location behind the liquid application nozzle in the moving direction, the rear camera configured to capture an image of a bubble formed in the liquid.

11. The weld inspection apparatus according to claim 3, wherein the liquid application head further comprises a rear camera disposed at a location behind the liquid application nozzle in the moving direction, the rear camera configured to capture an image of a bubble formed in the liquid.

12. The weld inspection apparatus according to claim 4, wherein the liquid application head further comprises a rear camera disposed at a location behind the liquid application nozzle in the moving direction, the rear camera configured to capture an image of a bubble formed in the liquid.

13. The weld inspection apparatus according to claim 6, wherein the liquid application head further comprises a rear camera disposed at a location behind the liquid application nozzle in the moving direction, the rear camera configured to capture an image of a bubble formed in the liquid.

14. The weld inspection apparatus according to claim 7, wherein the liquid application head further comprises a rear camera disposed at a location behind the liquid application nozzle in the moving direction, the rear camera configured to capture an image of a bubble formed in the liquid.

15. The weld inspection apparatus according to claim 8, wherein the liquid application head further comprises a rear camera disposed at a location behind the liquid application nozzle in the moving direction, the rear camera configured to capture an image of a bubble formed in the liquid.

16. The weld inspection apparatus according to claim 9, wherein the liquid application head further comprises a rear camera disposed at a location behind the liquid application nozzle in the moving direction, the rear camera configured to capture an image of a bubble formed in the liquid.

* * * * *